United States Patent

Gruber et al.

[11] Patent Number: 5,932,249
[45] Date of Patent: Aug. 3, 1999

[54] BUDESONIDE PELLETS WITH A CONTROLLED RELEASED PATTERN AND PROCESS FOR PRODUCING THE SAME

[75] Inventors: Peter Gruber, Bottmingen, Switzerland; Hans Joachim Lach, Bahlingen; Norbert Otterbeck, Uberlingen, both of Germany

[73] Assignee: Dr. Falk Pharma GmbH, Freiburg, Germany

[21] Appl. No.: 08/619,556

[22] PCT Filed: Jul. 29, 1994

[86] PCT No.: PCT/EP94/02531

§ 371 Date: Jul. 15, 1996

§ 102(e) Date: Jul. 15, 1996

[87] PCT Pub. No.: WO95/08323

PCT Pub. Date: Mar. 30, 1995

[30] Foreign Application Priority Data

Sep. 23, 1993 [DE] Germany ............... 43 32 394

[51] Int. Cl.[6] ............................................. A61K 9/14
[52] U.S. Cl. .................. 424/489; 424/490; 424/485; 424/462; 424/473
[58] Field of Search .................. 424/489, 473, 424/488, 485, 462

[56] References Cited

U.S. PATENT DOCUMENTS

| 5,188,836 | 2/1993 | Muhammad et al. | 424/431 |
| 5,213,808 | 5/1993 | Bar-Shalom et al. | 424/473 |
| 5,643,602 | 7/1997 | Ulmius | 424/462 |
| 5,681,584 | 10/1997 | Savastano et al. | 424/473 |

FOREIGN PATENT DOCUMENTS

| 0145558 | 6/1985 | European Pat. Off. . |
| 0453001 | 10/1991 | European Pat. Off. . |
| 2453640 | 11/1980 | France . |
| 9107172 | 5/1991 | WIPO . |

*Primary Examiner*—Neil S. Levy
*Assistant Examiner*—William E. Benston, Jr.
*Attorney, Agent, or Firm*—Fulbright & Jaworski, LLP.

[57] ABSTRACT

Disclosed are budesonide pellets with a controlled release pattern containing, from the inside to the outside: a) neutral pellets; b) an active principle layer of micronized budesonide and one or more water-soluble auxiliaries; c) a first lacquer coating consisting of 80 to 97% of at least one lacquer insoluble in gastric fluids but soluble in intestinal fluids and 3 to 20% of at least one lacquer insoluble in both gastric and intestinal fluids; and d) a second lacquer coating consisting of at least one lacquer insoluble in gastric and intestinal fluids. The invention also relates to a process for producing budesonide pellets with a controlled release pattern.

20 Claims, 2 Drawing Sheets

PRODUCTION OF 3mg BUDESONIDE CAPSULES

BUDESONIDE PELLETS WITH A CONTROLLED RELEASED PATTERN AND PROCESS FOR PRODUCING THE SAME

This application is a 371 of PCT/EP941/02531 filed Jul. 29, 1994.

The invention relates to budesonide pellets with controlled release profile and to a process for producing them. In particular, it relates to budesonide pellets with a release-controlling membrane comprising two separate lacquer layers.

Budesonide (16a, 17-butylidenedioxy-1b,21-dihydroxy-1,4-pregnadiene-3,20-dione) is a highly active corticosteroid which has been shown to be extremely effective for the treatment of inflammatory processes of the middle and lower intestinal tract. Thus, budesonide in oral slow-release form has brought about remission of active Crohn's disease and has few side effects on adrenocortical function (cf. the pilot study in "Der Kassenarzt, 13, pages 34 to 37, 1993"). A review of the pharmacological properties and the therapeutic efficacy of budesonide for asthma and rhinitis is given in "Drugs 44 (3), 375–407, 1992". The absorption of budesonide is low and it is subject to extensive first-pass metabolism. Since inflammatory processes often affect relatively large sections of the intestinal tract, there is a demand for a pharmaceutical form which spreads reproducibly over wide areas of the intestine and, moreover, releases the active substance only there.

An object of the invention is therefore to provide a pharmaceutical composition which ensures optimal distribution of the small amount of active substance (1 to 3 mg/dose) at the site of inflammation. Furthermore, the active substance is to be released neither in the stomach nor in the duodenum or the proximal jejunum but only from the middle jejunum onwards. From this section onwards there should be relatively rapid release (about 80 to 90% in 2 hours), differing distinctly from a slow-release form (for example 90% release in 6 to 8 hours).

Furthermore, a reproducible onset of action is to be ensured through rapid passage of the pharmaceutical composition through the stomach.

After a release-controlling shell has been detached, the sparingly soluble, very finely micronized active substance is to become rapidly resuspended in the intestinal fluid and display its effect on the inflamed mucosa. It is furthermore intended to provide a process for producing the pellets.

The invention is also in a process for producing budesonide pellets with a controlled release profile.

The various features of novelty which characterizes the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

The FIGURE schematically depicts a flow diagram for a process for producing the pellets of the invention.

This object is best achieved by pellets packed, for example, in hard gelatin capsules. After disintegration of the capsule in the stomach they are expelled into the intestine in accordance with the motility phase prevailing in the stomach at the time. This results in a distribution effect, and the active substance is able to display its effect on larger areas of the intestinal mucosa than a single-dose form.

Figure 1A:
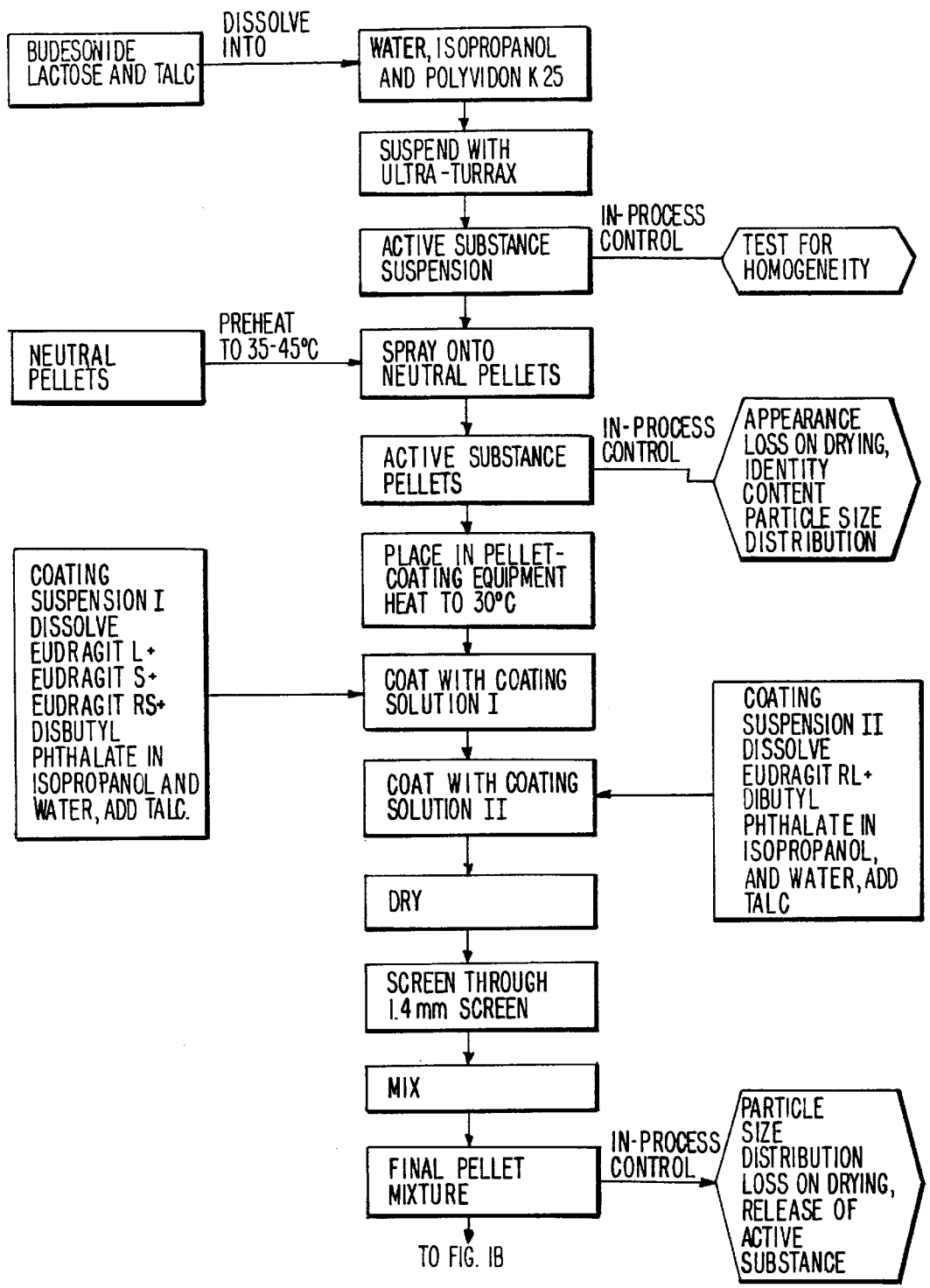

It has been found, surprisingly, that budesonide pellets with controlled release profile can be obtained when the active substance is enveloped by a release-controlling membrane comprising two separate lacquer layers, one lacquer layer I consisting of 80 to 97% of lacquers which are insoluble in gastric fluid and soluble in intestinal fluid and 3 to 20% of lacquers which are insoluble in gastric and intestinal fluids, and a lacquer layer II consisting of 100% lacquers which are insoluble in gastric and intestinal fluids.

The invention thus relates to budesonide pellets with controlled release profile, which are characterized in that they comprise, from the inside to the outside, a) neutral pellets b) an active substance layer comprising micronized budesonide and one or more water-soluble auxiliaries, c) a lacquer layer I comprising 80 to 97% of lacquers which are insoluble in gastric fluid and soluble in intestinal fluid and 3 to 20% of lacquers which are insoluble in gastric and intestinal fluids, in an amount of 4–16% by weight based on the lacquered active substance pellets (preferably 8–12%), and d) a lacquer layer II consisting of 100% lacquers which are insoluble in gastric and intestinal fluids.

The invention furthermore relates to a process for producing budesonide pellets with controlled release profile, which is characterized in that micronized budesonide is suspended as active substance in a solvent mixture consisting of alcohol:water from 0:100 to 20:80 with the addition of one or more water-soluble auxiliaries, the suspension is sprayed on to neutral pellets, after drying a lacquer suspension I consisting of 80 to 97% of lacquers which are insoluble in gastric fluid and soluble in intestinal fluid and 3 to 20% of lacquers which are insoluble in gastric and intestinal fluids are sprayed on, and after drying a lacquer suspension II consisting of 100% lacquers which are insoluble in gastric and intestinal fluids is sprayed on, and the active substance pellets are dried.

The pellets preferably comprise 75–95% by weight of neutral pellets, 0.4–20% by weight of the active substance layer, 4–16% by weight (more preferably 8–12% by weight) of lacquer layer I and 0.1–3% by weight (more preferably 0.5–1% by weight) of lacquer layer II, in each case based on lacquered active substance pellets.

Lacquer layer I preferably comprises Eudragit L, Eudragit S, Eudragit RS and Eudragit RL, and lacquer layer II preferably comprises Eudragit L and Eudragit RS. Moreover, the content in lacquer layer I of Eudragit L is 20 to 77%, preferably 40 to 50%, of Eudragit S is 20 to 77%, preferably 40 to 50%, of Eudragit RS, Eudragit RL is 3 to 20%, preferably 6 to 12%, where the total of Eudragit L and Eudragit S is 80 to 97%. The content of Eudragit RL and Eudragit RS in lacquer membrane II is 100%, with the proportion of RL being 0–100% and of RS being 100–0%.

The content of micronized budesonide per dose unit is 0.5–20 mg, preferably 0.5–5 mg, more preferably 0.6–3 mg. This corresponds to 0.1–20% by weight, preferably 0.1–5% by weight, more preferably 0.2–3% by weight of budesonide, based on the lacquered active substance pellets. Moreover a dose unit contains about 150–750 individual pellets. The particle size of the micronized budesonide is 5 to 25 $\mu$p, preferably about 10 micrometers ($\mu$m).

In order to achieve high local concentrations of active substance and spread of the active substance over an area of inflamed intestine which is as wide as possible, the dose of active substance has been distributed over hundreds of independent release-controlling pharmaceutical forms (pellets) which are about 1 mm in size (pellet distribution effect). The amount of active substance is preferably distributed over about 250 individual pellets. Moreover a pellet comprises 0.003 mg to 0.1 mg, preferably 0.004 mg, of budesonide. The pellets are suitably combined to give single dose units. For this purpose they can be enclosed by any desired pharmaceutically suitable envelope. The pellets can moreover be in the form of capsules, tablets, granules or in the form of sachets, which have been formulated in a conventional way. The pharmaceutical compositions may furthermore comprise formulation aids such as suspending agents, stabilizers and/or dispersants.

Eudragit L and S comprise acrylic/methacrylic acid copolymers with carboxyl groups, whereby these lacquers become soluble above pH 5.8 and 6.8 respectively.

More precisely, Eudragit L is a poly(methacrylic acid, methyl methacrylate) with a molar ratio of 1:1 and a molecular weight of 135,000 or a poly(ethyl acrylate, methacrylic acid) with a molar ratio of the monomeric units of 1:1 and a molecular weight of 250,000. Eudragit S is a poly (methacrylic acid, methyl methacrylate) with a molar ratio of the monomeric units of 1:2 and a molecular weight of 135,000.

Eudragit RS and RL are acrylic/methacrylic acid copolymers with quaternary ammonium groups. They are insoluble but swellable and subject to graded erosion in the pH range 1 to 7.

More precisely, Eudragit RL is a poly(ethyl acrylate, methyl methacrylate, trimethylammonioethyl methacrylate chloride) with a molar ratio of the monomer units of 1:2:0.2 and a molecular weight of 150,000. Eudragit RS is a poly(ethyl acrylate, methyl methacrylate, trimethylamonioethyl methacrylate chloride) with a molar ratio of 1:2:0.1 and a molecular weight of 150,000.

Active substance pellets are normally produced by stirring the active substance with an adhesive in an alcoholic liquid and spraying this suspension or solution onto so-called starter pellets. These starter pellets can be any desired pharmaceutically utilizable neutral pellets such as sugar/corn starch pellets. It is possible where appropriate to use other auxiliaries and formulation aids known to a skilled worker. However, testing the release of active substance revealed entirely unsatisfactory releases of active substance. Even after 4 hours in simulated intestinal fluid, less than 80% of the active substance had dissolved (see Comparative Example 1). Evidently the active substance is partly dissolved by the said solvents and forms a coherent, sparingly soluble layer on the pellets. This behavior is entirely unusual because only 3 mg of active substance were applied to 300 mg of starter pellets (1%).

Tests with water, in which the active substance dissolved virtually not at all, also lead to unsatisfactory releases (Comparative Example 2). Surprisingly, it was possible to find the required rapid release of active substance by suspending the active substance in a 0:100 to 20:80 alcohol:water solvent mixture and adding at least 2 parts of a water-soluble auxiliary to one part of active substance. The ratio 1 part of budesonide:4 parts of α-lactose monohydrate proved particularly advantageous in this connection. Other auxiliaries such as sucrose, sorbitol, mannitol, monosodium citrate etc. are also suitable (Example 1).

Economic considerations indicate that a release-controlling membrane on the pellets should not amount to more than 20% of the pellet weight.

Investigations with usual lacquers resistant to gastric fluid, such as cellulose acetate phthalate, hydroxypropylmethylcellulose phthalate and Eudragit L, however, showed that on testing the release of active substance at pH 6.8 release is too rapid even with 20% lacquer. As a consequence of the large surface area of the pellets, the lacquer is detached so rapidly that the release, substantiated from clinical investigations, of

| 0 to 2 hours | pH 1.2 | 0% release of active substance |
| 15 min | pH 6.8 | max. 5% release of active substance |
| 120 min | pH 6.8 | min. 90% release of active substance | was far from being reached. In all cases, the release after 15 min at pH 6.8 was already more than 50%. In addition, the amount of lacquer was unsatisfactorily high (20%).

A combination of Eudragit L with Eudragit S, which dissolves only at pH 7.0, also gave unsatisfactory results. Even with a Eudragit S:Eudragit L ratio of 8:2 it was not possible to reach the requirement (max. 5% after 15 min) (Comparative Example 3).

Addition of a third component, Eudragit RS, leads, with economically justifiable amounts of lacquer (about 10 to 15%), to a distinct reduction in the release of active substance at pH 6.8. With an amount of lacquer of 13.5% (Eudragit L:Eudragit S:Eudragit RS 46.5:46.5:7) at pH 6.8 there is release only of 5 to 10% within the first 15 minutes. Although increasing the Eudragit RS content to 12% achieves a reduction in release to below 5% after 15 minutes, surprisingly there is so great a reduction in the detachment of lacquer that after 120 min only about 70% is released (Examples 2 and 3). It is thus evident that every reduction of release of active substance in the first 15 min changes the nature of the lacquer membrane in such a way that the biologically important release requirement of min. 90% after 120 min can no longer be achieved. The above release profile which is necessary for medical reasons can, surprisingly, be achieved by a separate, second lacquer membrane.

For this purpose, the pellets produced as in Example 4 receive a second lacquer membrane comprising Eudragit RL. The amount is 0.1–3% (based on the lacquered active substance pellets). As Example 4 proves, the release of active substance after 15 minutes is 0%, but is already 81% after 60 minutes and 96% after 120 minutes. The second lacquer membrane is essential to the invention because it suppresses the release after 15 minutes to 0% with an inconsiderable reduction in the release after 120 minutes. This complicated release profile cannot be achieved with one of the mixtures shown in the comparative examples. The second lacquer membrane consists of Eudragit RL or RS or of mixtures of the two lacquers.

The said lacquers are dissolved as usual in alcohols such as ethanol, isopropanol and in acetone. As a rule, about 10% of plasticizer (based on lacquer dry matter) such as triacetin or dibutyl phthalate and talc are added to the lacquer solutions. The lacquer suspensions are, as a rule, sprayed using two-component nozzles in suitable coating equipment.

Figure 1B:
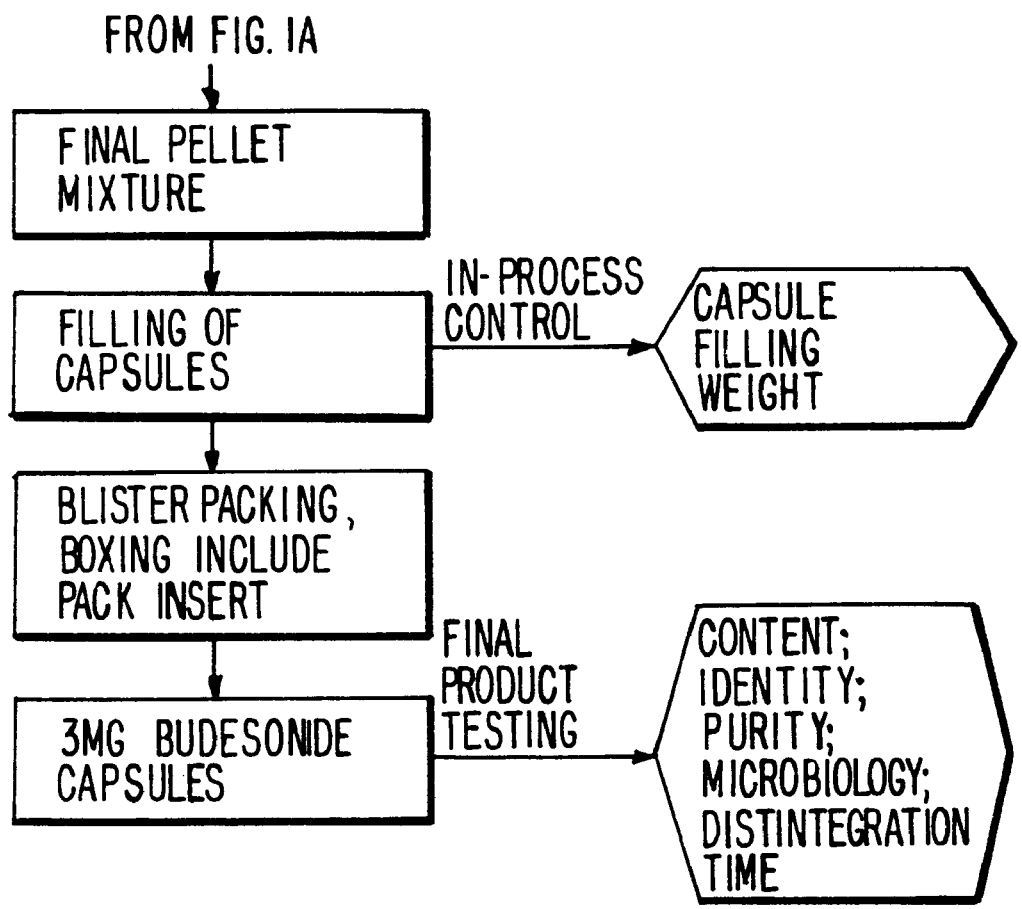

The production sequence is depicted in the flow diagram shown in FIG. 1. In principle, it comprises the adsorption of the active substance on inert starter pellets, the coating of the pellets with ph-dependent soluble or insoluble lacquers and the encapsulation of the pellets.

Variations in content of the order of 5 to 10% from batch to batch must be expected in the production of the active substance pellets. These variations make it necessary for the active substance content of the pellets to be determined before the encapsulation and to be taken into appropriate account when filling the capsules. The weight of capsule filling in a batch is calculated from the result of the budesonide content determinations on every batch of pellets. The weight is adjusted if required with the appropriate amount of neutral pellets.

The invention is explained in detail by means of the following examples.

Comparative Example 1

The release of active substance takes place under the following conditions:

Paddle method (USP XX II)
75 rpm, 37±0.5 degrees Celsius
Media
pH 1.2: 2 g of sodium chloride and 6.4 g of 37% strength HCl per 1000 ml of water
pH 6.8: 28 g of disodium hydrogen phosphate, anhydrous, and 4.34 g of citric acid per 1000 ml of water; adjusted to pH 6.8. 1.0 g of Myrj 53 is dissolved in 1000 ml of the buffer.

Composition of the pellets

| neutral pellets | (1) | 10.0 kg |
| Plasdone K 25 | (2) | 0.1 kg |
| talc | (3) | 0.4 kg |
| budesonide, micron. | (4) | 0.1 kg |
| | | 10.6 kg |

Component 2 is dissolved in 8 kg of 8:2 ethanol/water, and components 3 and 4 are suspended using an Ultra-Turrax. The suspension is sprayed onto the rotating neutral pellets in a pan by means of a two-component nozzle.

Release of active substance

| | pH 1.2 | pH 6.8 |
|---|---|---|
| 15 min | 24% | 18% |
| 30 min | 45% | 43% |
| 60 min | 59% | 61% |
| 120 min | 67% | 69% |
| 180 min | 74% | 73% |

Comparative Example 2

Budesonide active substance pellets are produced as in Comparative Example 1 with the difference that the active substance and the talc are suspended in an aqueous Plasdone solution (about 8 kg) and sprayed onto the neutral pellets.

Release of active substance

| | pH 6.8 |
|---|---|
| 15 min | 34% |
| 30 min | 48% |
| 60 min | 58% |
| 120 min | 65% |
| 180 min | 69% |
| Result: | |

Comparative Examples 1 and 2 show that the medically necessary release of minutes. 90% after 120 minutes at pH 6.8 cannot be achieved with these pellets.

EXAMPLE 1

| neutral pellets | (1) | 10.0 kg |
| Plasdone K 25 | (2) | 0.1 kg |
| talc | (3) | 0.4 kg |
| α-lactose monohydrate | (4) | 0.4 kg |
| budesonide, micronized | (5) | 0.1 kg |

Component 2 is dissolved in 3.3 kg of 9:1 water/ethanol, and components 3 to 5 are suspended using an Ultra-Turrax. The suspension is sprayed onto the neutral pellets in a rotating pan using a two-component nozzle.

Release of active substance

| | pH 1.2 | pH 6.8 |
|---|---|---|
| 15 min | 89.6% | 88.7% |
| 30 min | 98.1% | 98.4% |
| 60 min | 99.3% | 98.8% |
| 120 min | 99.5% | 99.1% |

Result

The active substance pellets released the active substance with optimal rapidity independently of the pH.

Comparative Example 3

Active substance pellets from Example 1 are sprayed as follows:

| active substance pellets | (1) | 5.50 kg |
| Eudragit S | (2) | 0.97 kg |
| Eudragit L | (3) | 0.24 kg |
| dibutyl phthalate | (4) | 0.12 kg |
| talc | (5) | 1.00 kg |

Components 2, 3, 4 are dissolved in 15 kg of 95:5 isopropanol/water, and talc is suspended in.

This lacquer suspension is sprayed onto 5.5 kg of active substance pellets in a rotating pan (amount of lacquer 22% based on starter pellets).

Release of active substance

| pH 1.2 | | pH 6.8 | |
|---|---|---|---|
| 60 min | 0% | 15 min | 42% |
| 120 min | 0% | 30 min | 83% |
| | | 60 min | 96% |

The pellets are first stirred at pH 1.2 for 120 min and then transferred quantitatively through a screen into buffer solution pH 6.8.

Result

The required release of max. 5% after 15 min at pH 6.8 cannot be achieved with economically justifiable amounts of lacquer (8:2 Eudragit S:Eudragit L lacquer combination).

EXAMPLE 2

5.5 kg of active substance pellets from Example 1 are sprayed with the following lacquer combination exactly as in Comparative Example 3:

| | |
|---|---|
| Eudragit S | 0.345 kg |
| Eudragit L | 0.345 kg |
| Eudragit RS | 0.052 kg |
| dibutyl phthalate | 0.070 kg |
| talc | 0.075 kg |

The lacquer components (Eudragit S:Eudragit L:Eudragit RS 46.5:46.5:7) are dissolved in 8.5 kg of 9:1 isopropanol/water and the subsequent procedure is as in Comparative Example 3.

Release of active substance

| pH 1.2 | | pH 6.8 | |
|---|---|---|---|
| 60 min | 0% | 15 min | 9.5% |
| 120 min | 0% | 30 min | 43.0% |
| | | 60 min | 75.0% |
| | | 120 min | 96.5% |

Result

The release of active substance after 15 min at pH 6.8 is distinctly reduced compared with Comparative Example 3 but does not yet reach the required value of max. 5% after 15 minutes at pH 6.8. The release after 120 minutes is above the tolerance limit (minutes. 90% after 120 minutes).

EXAMPLE 3

Active substance pellets from Example 1 are sprayed with the following lacquer combination exactly as in Example 2:

| | |
|---|---|
| Eudragit S | 0.327kg |
| Eudragit L | 0.327kg |
| Eudragit RS | 0.089kg |
| dibutyl phthalate | 0.070kg |
| talc | 0.075kg |

The lacquer components (Eudragit S:Eudragit L:Eudragit RS 44:44:12) are dissolved in 8.5 kg of 9:1 isopropanol/water and the subsequent procedure is as in Example 2.

Release of active substance

| pH 1.2 | | pH 6.8 | |
|---|---|---|---|
| 60 min | 0% | 15 min | 2.4% |
| 120 min | 0% | 30 min | 26.4% |
| | | 60 min | 56.3% |
| | | 120 min | 78.1% |
| | | 180 min | 89.8% |

Result

Increasing the Eudragit RS content to 12% pushes the release below 5% after 15 minutes at pH 6.8, but the release requirement after 120 minutes (minutes. 90%) is clearly not met.

EXAMPLE 4

5.5 kg of active substance pellets from Example 1 are sprayed with the following lacquer layers exactly as in Example 3:

Lacquer layer I

| | |
|---|---|
| Eudragit S | 0.304 kg |
| Eudragit L | 0.304 kg |
| Eudragit RS | 0.052 kg |
| dibutyl phthalate | 0.065 kg |
| talc | 0.065 kg |

The lacquer combination (Eudragit S:Eudragit L:Eudragit RS 46:46:8) is dissolved in 7.6 kg of 9:1 isopropanol/water and the subsequent procedure is as in Comparative Example 3. The amount of lacquer is 12%.

Release of active substance

| pH 1.2 | | pH 6.8 | |
|---|---|---|---|
| 60 min | 0% | 15min | 14.4% |
| 120 min | 0% | 30min | 49.0% |
| | | 60min | 84.0% |
| | | 120min | 98.4% |

Lacquer layer II

| | |
|---|---|
| Eudragit RL | 0.060kg |
| dibutyl phthalate | 0.070kg |
| talc | 0.100kg |

Eudragit RL is dissolved in 3.66 kg of 9:1 isopropanol/water and the plasticizer and talc are added by means of an Ultra-Turrax. The lacquer suspension is sprayed onto the pellets provided with lacquer layer I in a pan.

Release of active substance

| pH 1.2 | | pH 6.8 | |
|---|---|---|---|
| 60 min | 0% | 15 min | 0% |
| 120 min | 0% | 30 min | 28% |
| | | 60 min | 81% |
| | | 120 min | 97% |

Result

The second lacquer layer (0.92% Eudragit RL based on lacquered active substance pellets) reduces the release after 15 minutes at pH 6.8 to 0% as required while meeting the release requirement (minutes. 90% at 120 minutes). The combination of two lacquer layers proves to be considerably better than lacquer combinations of the lacquers mentioned for controlling release.

EXAMPLE 5

Active substance pellets are produced as in Example 1 containing three times the amount of active substance.

| | |
|---|---|
| neutral pellets | 10.0kg |
| Plasdone | 0.1kg |
| talc | 0.4kg |
| α-lactose monohydrate | 1.2kg |
| budeuonide, micron. | 0.3kg |
| | 12.0kg |

These pellets are sprayed with the following lacquer layers as described:

| Lacquer layer I | |
| --- | --- |
| Eudragit S | 0.49 kg |
| Eudragit L | 0.49 kg |
| Eudragit RL | 0.22 kg |
| dibutyl phthalate | 0.12 kg |
| talc | 0.18 kg |
| Lacquer layer II | |
| Eudragit RS | 0.081 kg |
| dibutyl phthalate | 0.01 kg |
| talc | 0.01 kg |

Release of active substance

| pH 1.2 | | pH 6.8 | |
| --- | --- | --- | --- |
| 60 min | 0% | 15 min | 1.8% |
| 120 min | 0% | 60 min | 75.3% |
| | | 120 min | 92.9% |

Result

The medically necessary release profile is likewise obtained with the lacquer combination (lacquer layer I) of Eudragit S:Eudragit L:Eudragit RL 41:41:18 (amount of lacquer 10%) and lacquer layer II with 0.59% Eudragit RS.

EXAMPLE 6
3 mg budesonide capsules

| | Composition | mg/capsule | function |
| --- | --- | --- | --- |
| 1) | budesonide, micr. | 3.0 | active substance |
| 2) | neutral pellets 1.0–1.18 mm | 300.0 | starter pellets |
| 3) | lactose monohydrate | 12.0 | filler |
| 4) | Plasdone K25 average MW 25,000 | 0.9 | binder |
| 5) | Eudragit L | 18.3 | lacquer |
| 6) | Eudragit S | 18.3 | lacquer |
| 7) | Eudragit RS | 3.0 | lacquer |
| 8) | Eudragit RL | 2.1 | lacquer |
| 9) | dibutyl phthalate | 4.2 | plasticizer |
| 10) | talc | 44.7 | release agent |
| | capsule contents | 406.5 | |
| 11) | hard gelatin capsule size I | 77.0 | |
| 12) | water*, purified | | approx. 69 mg |
| 13) | isopropanol* | | approx 409 mg |
| | Total capsule weight | 483.5 | |

*volatile constituents

EXAMPLE 7

| lacquered active substance | | |
| --- | --- | --- |
| pellets from Example 6 | (1) | 1.35 kg |
| microcrystalline cellulose | (2) | 4.00 kg |
| lactose, directly tablettable | (3) | 1.60 kg |
| silicon dioxide | (4) | 0.10 kg |
| magnesium stearate | (5) | 0.10 kg |
| | | 7.15 kg |

Components (2) to (4) are passed through a screen with a mesh width of 1.0 mm, and then component (1) is added and mixing is carried out for 10 minutes. Subsequently component (5) is added, and mixing is again carried out for 5 minutes. The mixture is compressed to tablets with a diameter of 13 mm. The weight of the tablet is 715 mg, and the budesonide content is 1 mg. The tablet disintegrates after 2 minutes, releasing the lacquered budesonide active substance pellets.

EXAMPLE 8

| lacquered active substance | | |
| --- | --- | --- |
| pellets from Example 6 | (1) | 8.13 kg |
| sorbitol instant granules | (2) | 40.00 kg |
| sodium carboxy-methylcellulose | (3) | 2.15 kg |
| citric acid | (4) | 0.90 kg |
| lemon flavor | (5) | 0.82 kg |
| | | 52.00 kg |

Components (2) to (4) are passed through a screen with a mesh width of 1.0 mm and mixed together with component (1) for 15 minutes. The mixture is packed in sachets each containing 2.6 g.

Before use, a sachet is suspended in a glass of water with stirring. The result is a pleasant-tasting drink in which there is scarcely any sedimentation of pellets, as a consequence of the increase in viscosity. A sachet contains 406.5 mg of pellets, which corresponds to 3 mg of budesonide.

EXAMPLE 9

375,000 hard gelatin capsules each containing 3 mg of budesonide were produced using the budesonide pellets according to the invention. The release profile was determined as in Comparative Example 1. The following values were obtained:

| 2h | pH 1.2 | 0% |
| --- | --- | --- |
| 15 min | pH 6.8 | 0% |
| 30 min | pH 6.8 | –55% |
| 60 min | pH 6.8 | >90% |

It will be understood that the specification and examples are illustrative but not limitative of the present invention and that other embodiments within the spirit and scope of the inventions will suggest themselves to those skilled in the art.

We claim:

1. Budesonide pellets with a controlled release profile, where the release of active substance is 0% after 15 minutes and at least 90% after 120 minutes, which pellets comprise, from the inside to the outside:

a) sugar spheres;

b) an active substance layer comprising micronized budesonide and one or more water-soluble auxiliaries;

c) a first lacquer layer comprising 80 to 97% of at least one lacquer which is insoluble in gastric fluid and soluble in intestinal fluid and 3 to 20% of at least one lacquer which is insoluble in gastric and intestinal fluids; and, d) a second lacquer consisting of 100% of at least one lacquer which is insoluble in gastric and intestinal fluids.

2. The budesonide pellets of claim 1 which, from the inside to the outside, comprise:

a) 75 to 95% by weight of sugar spheres;

b) 0.4 to 20% by weight of an active substance layer comprising micronized budesonide and one or more water-soluble auxiliaries;

c) 4 to 16% by weight of a first lacquer layer comprising 80 to 97% of at least one lacquer which is insoluble in gastric fluid and soluble in intestinal fluid and 3 to 20% of at least one lacquer which is insoluble in gastric and intestinal fluids; and, d) 0.1 to 3% by weight of a second lacquer layer consisting of 100% of at least one lacquer which is insoluble in gastric and intestinal fluids, in each case based on lacquered active substance pellets.

3. The pellets of claim 1 wherein the one or more water-soluble auxiliaries is selected from the group consisting of α-lactose monohydrate, sucrose, sorbitol, mannitol, and monosodium citrate.

4. The pellets of claim 1 wherein the budesonide content is 0.1 to 5% by weight based on lacquered active substance pellets.

5. The pellets of claim 1 wherein the particle size of the micronized budesonide is in the range of from 5 to 25 μm.

6. The pellets of claim 1 in the form of capsules, tablets or granules.

7. A process for producing budesonide pellets with a controlled release profile wherein the release of active substance is 0% after 15 minutes and at least 90% after 120 minutes, comprising:

a) suspending micronized budesonide as an active substance in a solvent mixture consisting of alcohol:water from 0:100 to 20:80 with the addition of one or more water-soluble auxiliaries to form a suspension;

b) the spraying the suspension onto sugar spheres;

c) drying the sprayed sugar spheres;

d) spraying the dried pellets with a first lacquer suspension consisting of 80 to 97% of at least one lacquer which is insoluble in gastric fluid and soluble in intestinal fluid and 3 to 20% of at least one lacquer which is insoluble in gastric and intestinal fluids;

e) drying the sprayed pellet;

f) spraying onto the pellets of e), a second lacquer suspension consisting of 100% of at least one lacquer which is insoluble in gastric and intestinal fluids; and, g) drying the active substance pellets.

8. The process of claim 7, wherein about 0.1–5 wt.-% of micronized budesonide is suspended in the solvent mixture and 4 to 16 wt.-% of the first lacquer suspension, based on lacquered active substance pellets, is sprayed on the sugar spheres, and 0.1 to 3 wt.-%, based on lacquered active substance pellets of the second lacquer is sprayed on, and the active substance pellets are dried.

9. The process of claim 7 wherein the water-soluble auxiliary is at least one selected from the group consisting of α-lactose monohydrate, sucrose, sorbitol, manitol and monosodium citrate.

10. The process of claim 7 wherein the budesonide content is about 0.1–5 wt.-% based on lacquered active substance pellets.

11. The process of claim 7 wherein the particle size of the micronized budesonide is in the range of from 5 to 25 μm.

12. The process of claim 7 wherein a suitable amount of pellet is packed in hard gelatin capsules or, with suitable auxiliaries, in sachets or compressed with suitable auxiliaries to tablets.

13. The pellets of claim 1, wherein the first lacquer layer comprises (i) a poly(methacrylic acid, methyl methacrylate) with a molar ratio of 1:1 and a molecular weight of 135,000 or a poly(ethyl acrylate, methacrylic acid) with a molar ratio of monomeric units of 1:1 and a molecular weight of 250,000; (ii) a poly(methacrylic acid, methyl methacrylate) with a molar ratio of monomeric units of 1:2 and a molecular weight of 135,000; (iii) a poly(ethylacrylate, methylmethacrylate, trimethyl ammonioethyl methacrylate chloride) with a molar ratio of 1:2:0.2 and a molecular weight of 150,000; and (iv) a poly(ethylacrylate, methyl methacrylate trimethyl ammonioethyl methacrylate chloride) with a molar ratio of 1:2:0.1 and a molecular weight of 150,000.

14. The pellets of claim 1, wherein the second lacquer layer comprises a poly(ethylacrylate, methylmethacrylate trimethyl ammonioethyl methacrylate chloride) with a molar ratio of 1:2:0.2 and a molecular weight of 150,000 and a poly(ethylacrylate, methylmethacrylate, trimethyl ammonioethyl methacrylate chloride) with a molar ratio of 1:2:0.1 and a molecular weight of 150,000.

15. The pellets of claim 1, wherein the first lacquer layer comprises (a) from 20% to 77% of a poly(methacrylic acid, methyl methacrylate) with a molar ratio of 1:1 and a molecular weight of 135,000 or a poly(ethylacrylate, methacrylic acid) with a molar ratio of monomeric units of 1:1 and a molecular weight of 250,000; (b) from 20% to 77% of a poly(methacrylic acid, methyl methacrylate) with a molar ratio of monomeric units of 1:2 and a molecular weight of 135,000, and (c) from 3% to 20% of a poly(ethylacrylate, methylmethacrylate, trimethyl ammonioethyl methacrylate chloride) with a molar ratio of 1:2:0.2 and a molecular weight of 150,000 and a poly(ethylacrylate, methylmethacrylate trimethyl ammonioethyl methacrylate chloride) with a molar ratio of 1:2:0.1 and a molecular weight of 150,000 wherein the total amount of (a) and (b), when combined, is 80% to 97%.

16. The pellets of claim 1, wherein the second layer comprises from 0% to 100% of a poly(ethylacrylate, methylmethacrylate, trimethyl ammonioethyl methacrylate chloride) with a molar ratio of 1:2:0.2 and a molecular weight of 150,000 and from 100% to 0% of a poly (ethylacrylate, methyl methacrylate trimethyl ammonioethyl methacrylate chloride) with a molar ratio of 1:2.0:0.1 and a molecular weight of 150,000.

17. The process of claim 7, wherein the first lacquer layer comprises at least one of (i) a poly(methacrylic acid, methyl methacrylate) with a molar ratio of 1:1 and a molecular weight of 135,000 or a poly-(ethyl acrylate, methacrylic acid) with a molar ratio of monomeric units of 1:1 and a molecular weight of 250,000; (ii) a poly(methacrylic acid, methyl methacrylate) with a molar ratio of monomeric units of 1:2 and a molecular weight of 135,000; (iii) a poly (ethylacrylate, methylmethacrylate, trimethyl ammonioethyl methacrylate chloride) with a molar ratio of 1:2:0.2 and a molecular weight of 150,000; and (iv) a poly(ethylacrylate, methyl methacrylate, trimethyl ammonioethyl methacrylate chloride) with a molar ratio of 1:2:0.1 and a molecular weight of 150,000.

18. The process of claim 7, wherein the second lacquer suspension comprises at least one of poly(ethylacrylate, methyl methacrylate, trimethyl ammonioethyl methacrylate chloride) with a molar ratio of 1:2:0.2 and a molecular weight of 150,000 and poly(ethylacrylate, methylmethacrylate, trimethyl ammonioethyl methacrylate chloride) with a molar ratio of 1:2:0.1 and a molecular weight of 150,000.

19. The process of claim 7, wherein the first lacquer suspension comprises (a) from 20% to 77% of a poly (methacrylic acid, methyl methacrylate) with a molar ratio of 1:1 and a molecular weight of 135,000 or a poly (ethylacrylate, methacrylic acid) with a molar ratio of monomeric units of 1:1 and a molecular weight of 250,000; (b) from 20% to 77% of a poly(methacrylic acid, methyl methacrylate) with a molar ratio of monomeric units of 1:2 and a molecular weight of 135,000, and (c) from 3% to 20% of a poly(ethylacrylate, methylmethacrylate, trimethyl ammonioethyl methacrylate chloride) with a molar ratio of 1:2:0.2 and a molecular weight of 150,000 and a poly (ethylacrylate, methylmethacrylate, trimethyl ammonioethyl methacrylate chloride) with a molar ratio of 1:2:0.1 and a molecular weight of 150,000 wherein the total amount of (a) and (b), when combined, is 80% to 97%.

20. The process of claim 7, wherein the second lacquer suspension comprises from 0–100% of a poly(ethylacrylate, methylmethacrylate, trimethyl ammonioethyl methacrylate chloride) with a ratio of 1:2.0:0.2 and a molecular weight of 150,000 and from 100% to 0% of a poly(ethylacrylate, methyl methacrylate, trimethyl ammonioethyl methacrylate chloride) with a molar ratio of 1:2.0:0.1 and a molecular weight of 150,000.

* * * * *